United States Patent [19]

Rowlands et al.

[11] 4,207,318
[45] * Jun. 10, 1980

[54] NOVEL IMIDAZOBENZOXAZINES

[75] Inventors: David A. Rowlands, Cirencester; John B. Taylor, Ampney Crucis Nr. Cirencester, both of England

[73] Assignee: Roussel Uclaf, Paris, France

[ * ] Notice: The portion of the term of this patent subsequent to Mar. 20, 1996, has been disclaimed.

[21] Appl. No.: 958,561

[22] Filed: Nov. 7, 1978

[30] Foreign Application Priority Data

Nov. 18, 1977 [GB] United Kingdom ............... 48178/77

[51] Int. Cl.$^2$ ................... A61K 31/535; C07D 498/02
[52] U.S. Cl. ............................... 424/248.4; 544/101; 544/105
[58] Field of Search ....................... 544/101; 424/248.4

[56] References Cited

U.S. PATENT DOCUMENTS

| | | | |
|---|---|---|---|
| 3,929,783 | 12/1975 | Krapcho et al. | 544/101 |
| 4,134,974 | 1/1979 | Melloni et al. | 544/101 X |
| 4,145,419 | 3/1979 | Rowlands et al. | 424/248.4 |

OTHER PUBLICATIONS

Pyatin et al., Chemical Abstracts, vol. 74, Abst. No. 112019x (1971).

Primary Examiner—John D. Randolph
Attorney, Agent, or Firm—Hammond & Littell, Weissenberger and Muserlian

[57] ABSTRACT

Novel imidazobenzoxazines of the formula

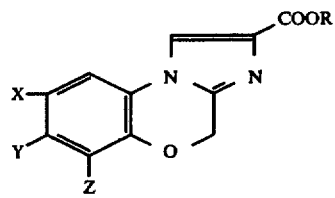

wherein X is selected from the group consisting of hydrogen, halogen and alkyl of 1 to 5 carbon atoms, R is selected from the group consisting of hydrogen, alkyl of 1 to 5 carbon atoms, and an equivalent of alkali metal, alkaline earth metal, magnesium, aluminum and nitrogen bases, Y is selected from the group consisting of hydrogen and alkyl of 1 to 5 carbon atoms, Z is selected from the group consisting of hydrogen and alkoxy of 1 to 5 carbon atoms with the proviso that at least one but not more than 2 of X, Y and Z are hydrogen, and their non-toxic, pharmaceutically acceptable acid addition salts having antiallergic and bronchodilatory activity and their preparation.

29 Claims, No Drawings

NOVEL IMIDAZOBENZOXAZINES

STATE OF THE ART

Novel imidazobenzoxazines are described in our copending, commonly assigned U.S. patent application Ser. No. 820,836 filed Aug. 1, 1977, now U.S. Pat. No. 4,145,419 and our copending, commonly assigned U.S. patent application Ser. No. 895,264 filed Apr. 10, 1978, now U.S. Pat. No. 4,151,280 describes novel pyrroloquinoxalines having antiallergic activity. Copending, commonly assigned U.S. patent application Ser. No. 869,842 filed Jan. 16, 1978 describes imidazoquinolines with antiallergic and bronchodilatory activity, and U.S. Pat. No. 4,075,343 describes also imidazoquinolines.

OBJECTS OF THE INVENTION

It is an object of the invention to provide the novel imidazobenzoxazines of formula I and their non-toxic, pharmaceutically acceptable acid addition salts.

It is a further object of the invention to provide a novel process for the preparation of the compounds of formula I.

It is an additional object of the invention to provide novel antiallergic and bronchodilatory compositions and to provide a method of combatting allergies in warm-blooded animals.

These and other objects of the invention will become obvious from the following detailed description.

THE INVENTION

The novel compounds of the invention have the formula

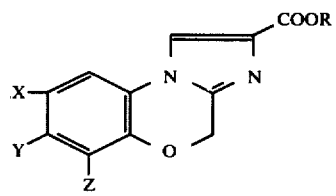

wherein X is selected from the group consisting of hydrogen, halogen and alkyl of 1 to 5 carbon atoms, R is selected from the group consisting of hydrogen, alkyl of 1 to 5 carbon atoms, and an equivalent of alkali metal, alkaline earth metal, magnesium, aluminum and nitrogen bases, Y is selected from the group consisting of hydrogen and alkyl of 1 to 5 carbon atoms, Z is selected from the group consisting of hydrogen and alkoxy of 1 to 5 carbon atoms with the proviso that at least one but not more than 2 of X, Y and Z are hydrogen and their non-toxic, pharmaceutically acceptable acid addition salts. Examples of Z are hydrogen and alkoxy such as methoxy, ethoxy, propoxy, isopropoxy and butyloxy. X and Y may also be alkyl such as methyl, ethyl, propyl, isopropyl, butyl and pentyl and X may be halogen such as fluorine, chlorine, bromine and iodine. Among the preferred compounds of formula I are those wherein X is chlorine, those wherein X is methyl, those wherein Y is methyl and those wherein Z is methoxy, those wherein Y is hydrogen, those wherein X is hydrogen, those wherein R is hydrogen and especially those wherein R and Z are both hydrogen.

Examples of R are hydrogen, alkyl such as methyl ethyl, propyl, isopropyl, butyl, pentyl, and an equivalent of alkali-metal such as sodium, potassium or lithium, alkali earth metal such as calcium, metal such as aluminium or magnesium, and amine such as lysine, arginine, triethanol amine or tris (hydroxymethyl) aminomethane.

Examples of suitable acids for the preparation of the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid tartaric acid, citric acid, oxalic acid, glyoxylic, aspartic acid, alkanesulfonic acids such as methanesulfonic acid and arylsulfonic acids such as benzenesulfonic acid.

It will be appreciated that, for pharmaceutical use the salts referred to above will be physiologically compatible salts but other salts may find use, for example, as intermediates in the preparation of compounds of formula I and their physiologically compatible salts.

Specific preferred compounds of formula I include 8-chloro-4H-imidazo-[2,1-c][1,4]-benzoxazine-2-carboxylic acid, 8-methyl-4H-imidazo-[2,1-c][1,4]-benzoxazine-2-carboxylic acid, 7-methyl-4H-imidazo-[2,1-c][1,4]-benzoxazine-2-carboxylic acid, 8-chloro-7-methyl-4H-imidazo-[2,1-c][1,4]-benzoxazine-2-carboxylic acid and non-toxic, pharmaceutically acceptable salts thereof.

The compounds of formula I may, for example, be prepared by the following processes, which processes constitute further features of the present invention:

A. For the preparation of compounds of formula I wherein X, Y and Z have the above definition and R is an alkyl of 1 to 5 carbon atoms, e.g. a methyl radical, the process comprises decarboxylation of a compound of the formula

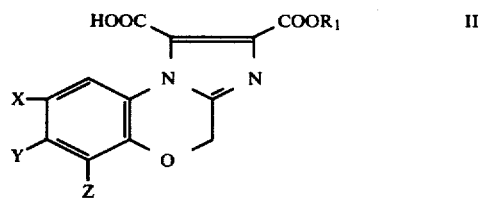

wherein $R_1$ is alkyl of 1 to 5 carbon atoms such as methyl which decarboxylation is preferably effected by heating the compound of formula II.

B. For the preparation of compounds of formula I wherein R is hydrogen, a compound of formula I wherein R is alkyl of 1 to 5 carbon atoms is subjected to hydrolysis such as in the presence of an aqueous solution of a base like sodium hydroxide or in the presence of an aqueous acid solution such as hydrochloric acid.

C. For the preparation of compounds of formula I wherein R is alkyl of 1 to 5 carbon atoms, an acid of formula I or a reactive derivative thereof is esterified with an alcohol of the formula HO—$R_1$ wherein $R_1$ is as defined above or a reactive derivative thereof. The reaction is preferably effected in an anhydrous organic solvent such as dichloromethane and if the acid is reacted with the alcohol, an activating agent such as dicyclohexylcarbodiimide is preferably present.

The compounds of formula I may be converted into their corresponding acid addition salts by reacting the free base with the desired acid. When R is hydrogen, the compounds of formula I may be converted into the desired salt by reaction with the desired inorganic or organic base.

The compounds of formula II, used as starting materials in the preparation of compounds of formula I, are themselves novel compounds and constitute a still further feature of the present invention. The compounds of formula II may, for example, be prepared by treatment of a compound of formula

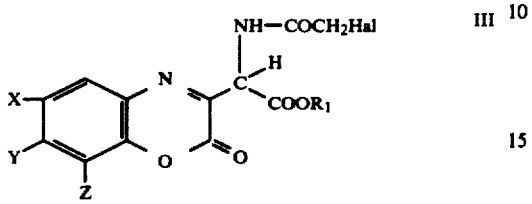

wherein X, Y, Z and $R_1$ are as hereinbefore defined and Hal is a halogen atom such as bromine, iodine or, more preferably, chlorine with a base, for example a weak base such as sodium carbonate followed by treatment with a strong acid, for example, concentrated hydrochloric acid. The compounds of formula III are also novel and constitute a yet further feature of the present invention.

The compounds of formula III may, for example, be obtained by reaction of a compound of formula IV

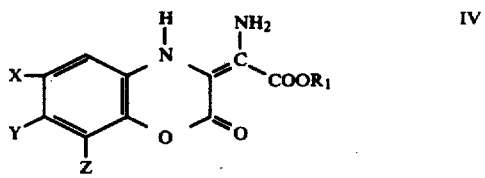

wherein X, Y, Z and $R_1$ are as hereinbefore defined with a haloacetyl halide such as chloroacetyl chloride. The reaction is preferably effected in an organic solvent such as dimethylformamide.

The compounds of formula IV may, for example, be prepared by hydrogenation of a compound of formula V

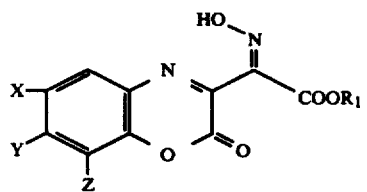

wherein X, Y, Z and $R_1$ are as hereinbefore defined, preferably in the presence of a noble metal catalyst such as platinum oxide.

The compounds of formula V may, if desired, be formed by reaction of a compound of formula VI

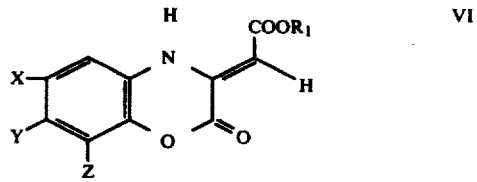

wherein X, Y, Z and $R_1$ are as hereinbefore defined with an organic nitrite, for example amyl nitrite, preferably in the presence of glacial acetic acid and trichloroacetic acid as solvent.

The compounds of formula VI may be obtained, if desired, by reaction of a compound of formula VII

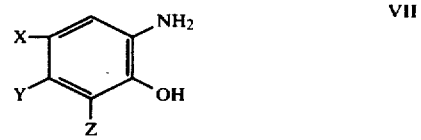

wherein X, Y and Z are as hereinbefore defined with a di-lower alkyl acetylenedicarboxylate, preferably at moderately elevated temperatures and preferably in the presence of a solvent such as ethanol.

The novel antiallergic compositions of the invention are comprised of an antiallergically effective amount of at least one compound of formula I and their non-toxic, pharmaceutically acceptable acid addition salts and an inert pharmaceutical carrier or excipient. The compositions may be in the form of tablets, dragees, granules, gelatin capsules, suppositories, syrups, aerosols, creams, ointments and injectable solutions or suspension. They are useful in the treatment of asthma and bronchial asthma of an allergic origin especially.

The active ingredient may be incorporated in excipients customarily employed in pharmaceutical compositions such as talc, gum arabic, lactose, starch, magnesium stearate, cocoa butter, aqueous or non-aqueous vehicles, fatty substances of animal or vegetable origin, paraffinic derivatives, glycols, various wetting dispersing or emulsifying agents and/or preservatives. Advantageously, the compositions may be formulated as dosage units with each unit being adapted to supply a fixed dose of active ingredient. Suitable dosage units for adults contain from 0.5 to 100 mg, preferably from 2 to 50 mg of active ingredient. The oral daily dosage, which may be varied according to the compound used, the subject treated and the complaint concerned, may, for example, be from 0.5 to 100 mg per day in adults.

The novel method of the invention for inducing antiallergic activity in warm-blooded animals including humans comprises administering to warm-blooded animals an antiallergically effective amount of at least one compound of formula I and their non-toxic, pharmaceutically acceptable acid addition salts. The compounds may be administered orally, rectally, topically or parenterally. The usual daily dose is 0.01 to 2 mg/kg depending on the compound and the method of administration.

In the following examples there are described several preferred embodiments to illustrate the invention. However, it should be understood that the invention is not intended to be limited to the specific embodiments.

EXAMPLE 1 methyl 8-chloro-4H-imidazo-[2,1-c][1,4]-benzoxazine-2-carboxylate

STEP A: methyl 6-chloro-2-oxo-2H-1,4-benzoxazine-$\Delta^{3(4H)}\alpha$-acetate 25 g (0.175 mol) of 2-amino-4-chlorophenol were dissolved in 400 ml of hot absolute ethanol and 29 g (0.204 mol) of dimethyl acetylenedicarboxylate were added thereto. The mixture obtained was warmed for half an hour and then was cooled in an ice-bath for two hours. The product thus formed was filtered off, washed with ether and finally dried under vacuum (over $P_2O_5$) to obtain 39.7 g (90% yield) of methyl 6-chloro-2-oxo-2H-1,4-benzoxazine-$\Delta^{3(4H)}\alpha$-acetate with a melting point of 169°–70° C. in the form of yellowish needles.

I.R. (KBr disc): 1225, 1292, 1612, 1638, 1662 and 1786 cm$^{-1}$.

Analysis: $C_{11}H_8NO_4Cl$; molecular weight=253.6: Calculated: %C 52.09, %H 3.18, %N 5.52, %Cl 13.98: Found: %C 51.92, %H 3.20, %N 5.57, %Cl 13.91.

STEP B: methyl 6-chloro-α-oximino-2-oxo-2H-1,4-benzoxazine-3-acetate 39.2 g (0.155 mol) of the methyl 6-chloro-2-oxo-2H-1,4-benzoxazine-$\Delta^{3(4H)}$-acetate prepared in Step A were suspended in 350 ml of glacial acetic acid and 6.3 g (0.0386 mol) of trichloroacetic acid and 19.5 (0.167 mol) of amyl nitrate were added thereto. The mixture obtained became warm and all the starting material dissolved. The resultant solution was left to stand at room temperature for one hour and then was cooled in an ice-bath for two hours. The product thus formed was filtered off and washed with ether until the filtrate was colorless and the resultant product was finally dried under vacuum (over $P_2O_5$) to obtain 35.7 g (81% yield) of methyl 6-chloro-α-oximino-2-oxo-2H-1,4-benzoxazine-3-acetate with a melting point of 176°–7° in the form of buff needles.

Analysis: $C_{11}H_7N_2O_5Cl$; molecular weight=282.6: Calculated: %C 46.74, %H 2.50, %N 9.91, %Cl 12.54: Found: %C 46.91: %H 2.58, %N 9.82, %Cl 12.58.

STEP C: methyl α-amino-6-chloro-2-oxo-2H-1,4-benzoxazine-$\Delta^{3(4H)}\alpha$-acetate 34.7 g (0.122 mol) of the methyl 6-chloro-α-oximino-2-oxo-2H-1,4-benzoxazine-3-acetate prepared in Step B were suspended in 400 ml of tetrahydrofuran dried over KOH pellets and 0.3 g of platinum oxide were added thereto. The mixture obtained was hydrogenated at up to 4 atmospheres pressure and the uptake of hydrogen was rapid and steady ceasing after about one and a half hours. The dark red solution thus formed was filtered through celite with the filter pad being well washed with chloroform. The filtrate was evaporated to dryness and the resultant product was triturated with ethanol/ether. The dark red crystalline product thus formed was filtered off and was washed with ethanol/ether before finally drying under vacuum over $P_2O_5$ to obtain 25.6 g (80% yield) of methyl α-amino-6-chloro-2-oxo-2H-1,4-benzoxazine-$\Delta^{3(4H)}\alpha$-acetate with a melting point of 203°–6° C. in the form of red needles.

I.R. (KBr disc): 1271, 1622, 1700, 1726, 3355 and 3475 cm$^{-1}$.

Analysis: $C_{11}H_9N_2O_4Cl$; molecular weight=268.6: Calculated: %C 49.18, %H 3.38, %N 10.43, %Cl 13.20: Found: %C 49.01, %H 3.39, %N 10.38, %Cl 13.41.

STEP D: methyl 2-chloroacetamido-2-(6-chloro-2-oxo-2H-1,4-benzoxazin-3-yl) acetate 9.43 g (35 mmol) of the methyl α-amino-6-chloro-2-oxo-2H-1,4-benzoxazine-$\Delta^{3(4H)}$-60 -acetate prepared in Step C were suspended in 200 ml of dimethylformamide and 5 g (45 mmol) of chloroacetyl chloride were added thereto. The starting material dissolved upon stirring and, after one hour, the reaction mixture was worked up in the usual manner with water/ethyl acetate. The combined ethyl acetate layers were dried, filtered and evaporated. The product thus obtained was triturated with ether and the resultant product was filtered off, washed with ether and dried under vacuum over $P_2O_5$ to obtain 10.8 g (89% yield) of methyl 2-chloroacetamido-2-(6-chloro-2-oxo-2H-1,4-benzoxazin-3-yl) acetate with a melting point of 170°–5° C. in the form of yellow needles.

I.R. (KBr disc): 1220, 1280, 1602, 1680, 1750, 1767 and 3250 cm$^{-1}$.

Analysis: $C_{13}H_{10}N_2O_5Cl_2$; molecular weight=345.1: Calculated: %C 45.24, %H 2.92, %N 8.12, %Cl 20.55: Found: %C 45.16, %H 2.94, %N 8.07, %Cl 20.57.

STEP E: 4H-8-chloro-2-methoxycarbonylimidazo-[2,1-c][1,4]-benzoxazine-1-carboxylic acid 8 g (23 mmol) of the methyl 2-chloroacetamido-2-(6-chloro-2-oxo-2H-1,4-benzoxazin-3-yl) acetate prepared in Step D were suspended in a mixture of 100 ml of ethanol and 500 ml of water and 12 g (0.113 mol) of sodium carbonate were added thereto. The mixture obtained was warmed on a water bath until a clear yellow solution was obtained and concentrated hydrochloric acid was then dripped slowly with stirring into the hot solution until a pH of 2–3 was obtained. A product crystallized out and after cooling, was filtered off, washed well with water and finally dried under vaccum over $P_2O_5$ to obtain 5.27 g (74% yield) of 4H-8-chloro-2-methoxycarbonylimidazo-[2,1-c][-benzoxazine-1-carboxylic acid with a melting point of 236°–8° C. (decarboxylates) in the form of buff needles.

I.R. (KBr disc): 1160, 1300, 1499, 1730, 2300 and 3600 cm$^{-1}$.

Analysis: $C_{13}H_9N_2O_5Cl$; molecularweight=308.7: Calculated: %C 50.58, %H 2.94, %N 9.07, %Cl 11.48: Found: %C 50.29, %H 2.91, %N 9.02, %Cl 11.48.

STEP F: methyl 8-chloro-4H-imidazo-[2,1-c][1,4]-benzoxazine-2-carboxylate 5.4 g (17.5 mmol) of the 4H-8-chloro-2-methoxycarbonyl-imidazo-[2,1-c][1,4]-benzoxazine-1-carboxylic acid prepared in Step E were stirred in 50 ml of Dowtherm A on an oil bath. The solution obtained bubbled vigorously when the oil bath reached 185°–195° C. When the effervescence had ceased, the solution was cooled and diluted with ether. The product crystallized out and was filtered off, washed well with ether and dried under vacuum over $P_2O_5$ to obtain 4.4 g (95% yield) of methyl 8-chloro-4H-imidazo-[2,1-c][1,4]-benzoxazine-2-carboxylate with a melting point of 239°–40° C. in the form of off-white needles.

I.R. (KBr disc): 1222, 1258, 1730 and 3135 cm$^{-1}$.

Analysis: $C_{12}H_9N_2O_3Cl$; molecular weight=264.7: Calculated: %C 54.46; %H 3.43, %N 10.58, %Cl 13.39: Found: %C 54.47, %H 3.48, %N 10.52, %Cl 13.43.

EXAMPLE 2 methyl 7-methyl-4H-imidazo-[2,1-c][1,4]-benzoxazine-2-carboxylate

STEP A: methyl 7-methyl-2-oxo-2H-1,4-benzoxazine-$\Delta^{3(4H)}\alpha$-acetate Using the procedure of Step A of Example 1 but using 2-amino-5-methyl-phenol as the starting material, methyl 7-methyl-2-oxo-2H-1,4-benzoxazine-$\Delta^{3(4H)}\alpha$-acetate with a melting point of 175°–6° C. was obtained.

STEP B: methyl 7-methyl-$\alpha$-oximino-2-oxo-2H-1,4-benzoxazine-3-acetate Using the procedure of Step B of Example 1, the product obtained in the preceding step was reacted to obtain methyl 7-methyl-$\alpha$-oximino-2-oxo-2H-1,4-benzoxazine-3-acetate with a melting point of 189°–90° C.

STEP C: methyl $\alpha$-amino-7-methyl-2-oxo-2H-1,4-benzoxazin-$\Delta^{3(4H)}\alpha$-acetate Using the procedure of Step C of Example 1, the product obtained in the preceding step was reacted to obtain methyl $\alpha$-amino-7-methyl-2-oxo-2H-1,4-benzoxazine-$\Delta^{3(4H)}\alpha$-acetate with a melting point of 140°–1° C.

STEP D: methyl 2-chloroacetamido-2-(7-methyl-2-oxo-2H-1,4-benzoxazin-3-yl) acetate Using the procedure of Step D of Example 1, the product obtained in the preceding step was reacted to obtain methyl 2-chloroacetamido-2-(7-methyl-2-oxo-2H-1,4-benzoxazin-3-yl) acetate with a melting point of 172°–3° C.

STEP E: 4H-7-methyl-2-methoxycarbonylimidazo-[2,1-c][1,4]-benzoxazine-1-carboxylic acid Using the procedure of Step E of Example 1, the product obtained in the preceding step was reacted to obtain 4H-7-methyl-2-methoxycarbonylimidazo-[2,1-c][1,4]-benzoxazine-1-carboxylic acid with a melting point of 176°–7° C.

STEP F: methyl 7-methyl-4H-imidazo-[2,1-c][1,4]-benzoxazine-2-carboxylate

Using the procedure of Step F of Example 1, the product obtained in the preceding step was reacted to obtain methyl 7-methyl-4H-imidazo-[2,1-c][1,4]-benzoxazine-2-carboxylate with a melting point of 180°–1° C.

I.R. (KBr disc): 1265, 1560, 1714 and 3140 cm$^{-1}$.
Analysis: $C_{13}H_{12}N_2O_3$; molecular weight = 244.3: Calculated: %C 63.93, %H 4.95, %N 11.47: Found: %C 63.95, %H 4.93, %N 11.47.

EXAMPLE 3 methyl 8-chloro-7-methyl-4H-imidazo-[2,1-c][1,4]benzoxazine-2-carboxylate

STEP A: methyl 6-chloro-5-methyl-2-oxo-2H-1,4-benzoxazine-$\Delta^{3(4H)}\alpha$-acetate Using the procedure of Step A of Example 1,2-amino-4-chloro-5-methylphenol as the starting material was reacted to obtain methyl 6-chloro-5-methyl-2-oxo-2H-1,4-bezoxazine-$\Delta^{3(4H)}\alpha$-acetate with a melting point of 195°–6° C.

STEP B: methyl 6-chloro-5-methyl-$\alpha$-oximino-2-oxo-2H-1,4-benzoxazine-3-acetate Using the procedure of Step B of Example 1, the product obtained in the preceding step was reacted to obtain methyl 6-chloro-5-methyl-$\alpha$-oximino-2-oxo-2H-1,4-benzoxazine-3-acetate with a melting point of 190°–1° C.

STEP C: methyl $\alpha$-amino-6-chloro-5-methyl-2-oxo-2H-1,4-benzoxazine-$\Delta^{3(4H)}\alpha$-acetate Using the procedure of Step C of Example 1, the product obtained in the preceding step was reacted to obtain methyl $\alpha$-amino-6-chloro-5-methyl-2-oxo-2H-1,4-benzoxazine-$\Delta^{3(4H)}\alpha$-acetate with a melting point of 163°–165° C.

STEP D: methyl 2-chloroacetamido-2-(6-chloro-5-methyl-2-oxo-2H-1,4-benzoxazin-3-yl) acetate Using the procedure of Step D of Example 1, the product obtained in the preceding step was reacted to obtain methyl 2-chloroacetamido-2-(6-chloro-5-methyl-2-oxo-2H-1,4-benzoxazin-3-yl) acetate with a melting point of 184°–186° C.

STEP E: 4H-8-chloro-7-methyl-2-methoxycarbonylimidazo-[2,1-c] [1,4]-benzoxazine-1-carboxylic acid Using the procedure of Step E of Example 1, the product obtained in the preceding step was reacted to obtain 4H-8-chloro-7-methyl-2-methoxycarbonylimidazo-[2,1-c][1,4]-benzoxazine-1-carboxylic acid with a melting point of 240°–244° C.

STEP F: methyl 8-chloro-7-methyl-4H-imidazo-[2,1-c][1,4]-benzoxazine-2-carboxylate Using the procedure of Step F of Example 1, the product obtained in the preceding step was reacted to obtain methyl 8-chloro-7-methyl-4H-imidazo-[2,1-c][1,4]-benzoxazine-2-carboxylate with a melting point of 242°–246° C.

I.R. (KBr disc): 760, 1281, 1560, 1721 and 3135 cm$^{-1}$.
Analysis: $C_{13}H_{11}N_2O_3Cl$; molecular weight = 278.7: Calculated: %C 56.03, %H 3.98, %N 10.05, %Cl 12.72. Found: %C 55.81, %H 3.99, %N 10.07, %Cl 12.77.

The 2-amino-4-chloro-5-methylphenol used in Step A was prepared by catalytic hydrogenation of 4-chloro-5-methyl-2-nitrophenol.

EXAMPLE 4 methyl 6-methoxy-4H-imidazo-[2,1-c][1,4]-benzoxazine-2-carboxylate

STEP A: methyl 8-methoxy-2-oxo-2H-1,4-benzoxazine-$\Delta^{3(4H)}\alpha$-acetate Using the procedure of Step A of Example 1, 2-amino-6-methoxy-phenol as the starting material was reacted to obtain methyl 8-methoxy-2-oxo-1,4-benzoxazine-$\Delta^{3(4H)}\alpha$-acetate with a melting point of 197°–199° C.

STEP B: methyl 8-methoxy-α-oximino-2-oxo-2H-1,4-benzoxazine-3-acetate

Using the procedure of Step B of Example 1, the product obtained in the previous step was reacted to obtain methyl 8-methoxy-α-oximino-2-oxo-2H-1,4-benzoxazine-3-acetate with a melting point of 176°–178° C.

STEP C: methyl α-amino-8-methoxy-2-oxo-2H-1,4-benzoxazine-$\Delta^{3(4H)}\alpha$-acetate Using the procedure of Step C of Example 1, the product obtained in the previous step was reacted to obtain methyl α-amino-8-methoxy-2-oxo-2H-1,4-benzoxazine-$\Delta^{3(4H)}\alpha$-acetate with a melting point of 182°–184° C.

STEP D: methyl 2-chloroacetamido-2-(8-methoxy-2-oxo-2H-1,4-benzoxazin-3-yl) acetate Using the procedure of Step D of Example 1, the product obtained in the previous step was reacted to obtain methyl 2-chloroacetamido-2-(8-methoxy-2-oxo-2H-1,4-benzoxazin-3-yl) acetate with a melting point of 152°–154° C.

STEP E: 6-methoxy-2-methoxycarbonylimidazo-[2,1-c][1,4]-benzoxazine-1-carboxylic acid Using the procedure of Step E of Example 1, the product obtained in the preceding step was reacted to obtain 6-methoxy-2-methoxycarbonylimidazo-[2,1-c][1,4]-benzoxazine-1-carboxylic acid with a melting point of 167°–168° C.

STEP F: methyl 6-methoxy-4H-imidazo-[2,1-c][1,4]-benzoxazine-2-carboxylate

Using the procedure of Step F of Example 1, the product obtained in the preceding step was reacted to obtain methyl 6-methoxy-4H-imidazo[2,1-c][1,4]-benzoxazine-2-carboxylate with a melting point of 188°–190° C.

I.R. (KBr disc): 770, 1217, 1499, 1541, 1704 and 3140 cm$^{-1}$.

Analysis: $C_{13}H_{12}N_2O_4$; molecular weight=260.3: Calculated: %C 60.00, %H 4.65, %N 10.76: Found: %C 59.97, %H 4.67, %N 10.79.

The 2-amino-6-methoxyphenol used in Step A was prepared by catalytic hydrogenation of 6-methoxy-2-nitrophenol.

EXAMPLE 5 methyl 8-methyl-4H-imidazo-[2,1-c][1,4]-benzoxazine-2-carboxylate

STEP A: methyl 6-methyl-2-oxo-2H-1,4-benzoxazine-$\Delta^{3(4H)}\alpha$-acetate Using the procedure of Step A of Example 1, 2-amino-4-methylphenol as the starting material was reacted to obtain methyl 6-methyl-2-oxo-2H-1,4-benzoxazine-$\Delta^{3(4H)}\alpha$-acetate with a melting point of 141°–142° C.

STEP B: methyl 6-methyl-α-oximino-2-oxo-2H-1,4-benzoxazine-3-acetate

Using the procedure of Example B of Example 1, the product obtained in the preceding step was reacted to obtain methyl 6-methyl-α-oximino-2-oxo-2H-1,4-benzoxazine-3-acetate with a melting point of 176°–177° C.

STEP C: methyl α-amino-6-methyl-2-oxo-2H-1,4-benzoxazine-$\Delta^{3(4H)}\alpha$-acetate Using the procedure of Step C of Example 1, the product obtained in the preceding step was reacted to obtain methyl α-amino-6-methyl-2-oxo-2H-1,4-benzoxazine-$\Delta^{3(4H)}\alpha$-acetate with a melting point of 145°–146° C.

STEP D: methyl 2-chloroacetamido-2-(6-methyl-2-oxo-2H-1,4-benzoxazine-3-yl) acetate Using the procedure of Step D of Example 1, the product obtained in the preceding step was reacted to obtain methyl 2-chloroacetamido-2-(6-methyl-2-oxo-2H-1,4-benzoxazin-3-yl) acetate with a melting point of 160°–165° C.

STEP E: 4H-8-methyl-2-methoxycarbonylimidazo-[2,1-c][1,4]benzoxazine-1-carboxylic acid Using the procedure of Step E of Example 1, the product obtained in the preceding step was reacted to obtain 4H-8-methyl-2-methoxycarbonylimidazo-[2,1-c][1,4]-benzoxazine-1-carboxylic acid with a melting point of 178°–179° C.

STEP F: methyl 8-methyl-4H-imidazo-[2,1-c][1,4]-benzoxazine-2-carboxylate

The 4H-8-methyl-2-methoxycarbonyl-imidazo-[2,1-c][1,4]-benzoxazine-1-carboxylic acid obtained in the previous step was stirred in a flask in an oil bath at 200°–210° C. After effervescence had ceased, the flask was cooled and chloroform was added thereto. The chloroform solution was then chromatographed over a silica column and the fractions containing the product were collected, combined and evaporated. Trituration with ether gave 4.65 g (86% yield) of methyl 8-methyl-4H-imidazo-[2,1-c][1,4]-benzoxazine-2-carboxylate in the form of colorless needles with a melting point of 195°–197° C.

I.R. (KBr disc): 1206, 1260, 1709 and 3135 cm$^{-1}$.

Analysis: $C_{13}H_{12}N_2O_3$; molecular weight=244.3 Calculated: %C 63.93, %H 4.95, %N 11.47: Found: %C 63.88, %H 5.00, %N 11.45.

EXAMPLE 6

8-chloro-4H-imidazo-[2,1-c][1,4]-benzoxazine-2-carboxylic acid

The methyl 8-chloro-4H-imidazo-[2,1-c][1,4]-benzoxazine-2-carboxylate prepared in Example 1 was suspended in 50 ml of ethanol and a solution of 1.15 g (29 mmol) of sodium hydroxide in 50 ml of water was added thereto. The mixture obtained was then heated on a steam bath until a clear solution was obtained and thin layer chromatography indicated no starting ester remaining. The solution was filtered and the filtrate was acidified while still hot to a pH of 2–3 with concentrated hydrochloric acid. On cooling, the acid crystallized out and was collected, was washed with water and dried over $P_2O_5$ under vacuum to obtain 3.20 g (97% yield) of 8-chloro-4H-imidazo-[2,1-c][1,4]-benzoxazine-2-carboxylic acid in the form of colorless needles with a melting point of 276°–278° C.

I.R. (KBr disc): 1260, 1509, 1565, 1700, 2100–3500 and 3155 cm$^{-1}$.

Analysis: $C_{11}H_7N_2O_3Cl$; molecular weight=250.6: Calculated: %C 52.71, %H 2.82, %N 11.18, %Cl 14.14: Found: %C 52.62, %H 2.84, %N 11.12, %Cl 14.20.

EXAMPLE 7

7-methyl-4H-imidazo-[2,1-c][1,4]-benzoxazine-b 2-carboxylic acid

Using the procedure of Example 6, methyl 7-methyl-4H-imidazo[2,1-c][1,4]-benzoxazine-2-carboxylate was reacted to obtain 7-methyl-4H-imidazo-[2,1-c][1,4]-benzoxazine-2-carboxylic acid, with a melting point of 278°–279° C.

I.R. (KBr disc): 1130–1260, 1550, 1730, 2100–3600 and 3145 cm$^{-1}$.

Analysis: $C_{12}H_{10}N_2O_3$; molecular weight=230.2: Calculated: %C 62.61, %H 4.38, %N 12.17: Found: %C 62.42, %H 4.59, %N 12.13.

EXAMPLE 8

8-chloro-7-methyl-4H-imidazo-[2,1-c][1,4]-benzoxazine-2-carboxylic acid

Using the procedure of Example 6, methyl 8-chloro-7-methyl-4H-imidazo-[2,1-c][1,4]-benzoxazine-2-carboxylate was reacted to obtain 8-chloro-7-methyl-4H-imidazo-[2,1-c][1,4]benzoxazine-2-carboxylic acid with a melting point of 285°–286° C.

I.R. (KBr disc): 1280, 1519, 1566, 1691, 2300–3600 and 3145 cm$^{-1}$.

Analysis: $C_{12}H_9N_2O_3Cl$; molecular weight=264.7: Calculated: %C 54.46, %H 3.43, %N 10.58, %Cl 13.39: Found: %C 54.35, %H 3.57, %N 10.36, %Cl 13.40.

EXAMPLE 9

6-methoxy-4H-imidazo-[2,1-c][1,4]-benzoxazine-2-carboxylic acid

Using the procedure of Example 6, methyl 6-methoxy-4H-imidazo-[2,1-c][1,4]-benzoxazine-2-carboxylate was reacted to obtain 6-methoxy-4H-imidazo-[2,1-c][1,4]-benzoxazine-2-carboxylic acid with a melting point of 275°–277° C.

I.R. (KBr disc): 1217, 1230, 1276, 1695, 2100–3200 and 3135 cm$^{-1}$.

Analysis: $C_{12}H_{10}N_2O_4$; molecular weight=246.2: Calculated: %C 58.54, %H 4.09, %N 11.38: Found: %C 58.24, %H 4.17, %N 11.36.

EXAMPLE 10

8-methyl-4H-imidazo-[2,1-c][1,4]-benzoxazine-2-carboxylic acid

Using the procedure of Example 6, methyl 8-methyl-4H-imidazo-[2,1-c][1,4]-benzoxazine-2-carboxylate was reacted to obtain 8-methyl-4H-imidazo-[2,1-c][1,4]-benzoxazine-2-carboxylic acid with a melting point of 281°–285° C.

I.R. (KBr disc): 1192, 1249, 1719, 2100–3600 and 3160 cm$^{-1}$.

Analysis: $C_{12}H_{10}N_2O_3$; molecular weight=230.2: Calculated: %C 62.61, %H 4.38, %N 12.17: Found: %C 62.26, %H 4.60, %N 12.07.

EXAMPLE 11

Tablets were prepared containing 5 mg of 8-methyl-4H-imidazo-[2,1-c][1,4]-benzoxazine-2-carboxylic acid and sufficient excipient of lactose, talc, starch and magnesium stearate to obtain a final tablet weight of 100 mg.

A metered dose aerosol dispenser was packed with the following ingredients per dose: 5 mg of 8-methyl-4H-imidazo-[2,1-c][1,4]-benzoxazine-2-carboxylic acid, 0.15 mg of emulsifier and a sufficient quantity of propellant, to obtain a final weight of 50 mg.

PHARMACOLOGICAL STUDY

Passive cutaneous anaphylaxis (PCA) in rats

The following compounds were tested for their physiological activity in the test: methyl 8-chloro-4H-imidazo-[2,1-c][1,4]-benzoxazine-2-carboxylate (compound A), methyl 8-methyl-4H-imidazo-[2,1-c][1,4]-benzoxazine-2-carboxylate (compound B), 8-chloro-4H-imidazo-[2,1-c][1,4]-benzoxazine-2-carboxylic acid (compound C), 7-methyl-4H-imidazo-[2,1-c][1,4]-benzoxazine-2-carboxylic acid (compound D), 8-chloro-7-methyl-4H-imidazo-[2,1-c][1,4]-benzoxazine-2-carboxylic acid (compound E), 6-methoxy-4H-imidazo-[2,1-c][1,4]-benzoxazine-2-carboxylic acid (compound F) and 8-methyl-4H-imidazo-[2,1-c][1,4]-benzoxazine-2-carboxylic acid (compound G).

Cutaneous anaphylaxis was induced in rats by intradermal (ID) sensitization with antiserum followed three days later by systemic challenge with antigen. Evans blue dye injected with the antigen is used as a marker to assess the severity of the local response. Anti-allergic drugs inhibit this reaction. This method has been described by OVARY (1962) "Passive Cutaneous Anaphylaxis in Allergology" Page 358–367 Ed. Brown: Pergamon Press. Animals: -male rats weighing 180–220 grams are used in groups of seven.

Preparation of Antigen for Sensitization (Alum precipitated ovalbumen)

1. Wash 120 grams of $Al(OH)_3$ gel in 140 ml of saline (use of a macerater facilitates mixing).
2. Centrifuge at 3,000 rpm for about 10 minutes.
3. Resuspend the precipitate with 300 ml of albumen egg powder (1.3 mg/ml) in saline and allow to stand for 30 minutes.
4. Centrifuge at 3,000 rpm for 10 minutes.
5. Weigh the wet precipitate and to each gram weight add 1 ml of saline. Store in refrigerator (Quantity sufficient for 60 rats for a 3 day sensitization program).

Preparation of Antiserum (anti-ovalbumen)

1 ml of the alum precipitated ovalbumen was injected subcutaneously into rats weighing 180–200 grams on days 0,2,4. The rats were bled on day 14 either by cardiac puncture or via the dorsal abdominal aorta. Equal quantities of serum from each animal were pooled and thoroughly mixed and 2 ml aliquots were stored at −20° C. in plastic tubes.

Serum Dilution for PCA

The antiserum for sensitization was diluted so that an ID injection of 0.1 ml into control animals would give an average score of a single spot of between 2.0–3.5 using 5 point scoring system.

Method (A) SENSITIZATION: The rats were anaesthetized Nembutal (40–60 mg/kg i.p) and were then sensitized by four ID injections (0.1 ml each) on their shaved backs. The animals were then left for a period of three days to develop sensitization.

(B) CHALLENGE: The sensitized rats were dosed orally or intraveneously with the drug immediately prior to intraveneous challenge via the superficial penile vein with 1 ml of an antigen/Evans blue mixture (1 mg albumen egg powder in 0.5 ml saline plus 0.5 ml of 1% Evans blue). The injections were speeded up by using an automatic 1 ml self-filling glass syringe. The "challenged" rats were killed after 30 minutes, (usually pithed) and their skin on the dorsal surface was removed. The degree and area of blueing, proportional to the anaphylactic reaction was assessed on a five point scoring system.

Calculations

1. Total scores for sites 1,2,3 and $4 = X$
2. Mean value of X for each group $= \overline{X}$
3. $\overline{X} t = \overline{X}$ for test group
   $\overline{X} c = \overline{X}$ for control group 4. % inhibition $= \dfrac{\overline{X}c - \overline{X}t}{\overline{X}c} \times \dfrac{100}{1}$ 5. $ED_{50} = $ dose of drug giving 50% inhibition.

$ED_{50}$ values for the compounds tested in the passive cutaneous anaphylaxis screen (in rats) are as follows:

| Compound | ED$_{50}$ mg/kg I.V. | mg/kg P.O. |
|---|---|---|
| A | — | 2.79 |
| B | — | 1.46 |
| C | 0.42 | 0.13 |
| D | 0.39 | 4.0 |
| E | 0.75 | — |
| F | 3.27 | — |
| G | 0.35 | 0.37 |

Various modifications of the compounds and methods of the invention may be made without departing from the spirit or scope thereof and it is to be understood that the invention is intended to be limited only as defined in the appended claims.

We claim:
1. A compound of the formula

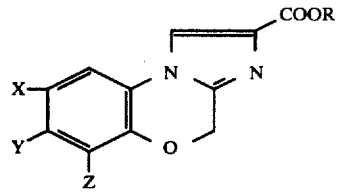

wherein X is selected from the group consisting of hydrogen, halogen and alkyl of 1 to 5 carbon atoms, R is selected from the group consisting of hydrogen, alkyl of 1 to 5 carbon atoms, alkali metal, alkaline earth metal, magnesium, aluminum and nitrogen bases, Y is selected from the group consisting of hydrogen and alkyl of 1 to 5 carbon atoms, Z is selected from the group consisting of hydrogen and alkoxy of 1 to 5 carbon atoms with the proviso that at least one but not more than 2 of X, Y and Z are hydrogen and their non-toxic, pharmaceutically acceptable acid addition salts.

2. A compound of claim 1 wherein X is selected from the group consisting of chlorine and methyl.

3. A compound of claim 1 wherein Y is methyl.

4. A compound of claim 1 wherein Z is methoxy.

5. A compound of claim 1 wherein R is hydrogen.

6. A compound of claim 1 wherein Z is hydrogen.

7. A compound of claim 1 wherein R and Z are hydrogen.

8. A compound of claim 1 wherein X is selected from the group consisting of hydrogen, chlorine and methyl and Y is selected from the group consisting of hydrogen and methyl.

9. A compound of claim 1 selected from the group consisting of 8-chloro-4H-imidazo-[2,1-c][1,4]-benzoxazine-2-carboxylic acid and its non-toxic, pharmaceutically acceptable salts.

10. A compound of claim 1 selected from the group consisting of 8-methyl-4H-imidazo-[2,1-c][1,4]-benzoxazine-2-carboxylic acid and its non-toxic, pharmaceutically acceptable salts.

11. A compound of claim 1 selected from the group consisting of 7-methyl-4H-imidazo-[2,1-c][1,4]-benzoxazine-2-carboxylic acid and its non-toxic, pharmaceutically acceptable salts.

12. A compound of claim 1 selected from the group consisting of 8-chloro-7-methyl-4H-imidazo-[2,1-c][1,4]-benzoxazine-2-carboxylic acid and its non-toxic pharmaceutically acceptable salts.

13. An antiallergic composition comprising an antiallergically effective amount of at least one compound of claim 1 and a pharmaceutical carrier.

14. A composition of claim 13 selected from the group consisting of 8-chloro-4H-imidazo-[2,1-c][1,4]-benzoxazine-2-carboxylic acid and its non-toxic, pharmaceutically acceptable salts.

15. A composition of claim 13 selected from the group consisting of 8-methyl-4H-imidazo-[2,1-c][1,4]-benzoxazine-2-carboxylic acid and its non-toxic, pharmaceutically acceptable salts.

16. A composition of claim 13 selected from the group consisting of 7-methyl-4H-imidazo-2,1-c][1,4]-benzoxazine-2-carboxylic acid and its non-toxic, pharmaceutically acceptable salts.

17. A composition of claim 13 selected from the group consisting of 8-chloro-7-methyl-4H-imidazo-[2,1-c][1,4]-benzoxazine-2-carboxylic acid and its non-toxic, pharmaceutically acceptable salts.

18. A method of relieving allergic symptoms in warm-blooded animals comprising administering to warm-blooded animals an antiallergically effective amount of at least one compound of claim 1.

19. A method of claim 18 wherein X is selected from the group consisting of chlorine and methyl.

20. A method of claim 18 wherein Y is methyl.

21. A method of claim 18 wherein Z is methoxy.

22. A method of claim 18 wherein R is hydrogen.

23. A method of claim 18 wherein Z is hydrogen.

24. A method of claim 18 wherein R and Z are hydrogen.

25. A method of claim 18 wherein X is selected from the group consisting of hydrogen, chlorine and methyl and Y is selected from the group consisting of hydrogen and methyl.

26. A method of claim 18 selected from the group consisting of 8-chloro-4H-imidazo-[2,1-c][1,4]-benzoxazine-2-carboxylic acid and its non-toxic, pharmaceutically acceptable salts.

27. A method of claim 18 selected from the group consisting of 8-methyl-4H-imidazo-[2,1-c][1,4]-benzoxazine-2-carboxylic acid and its non-toxic, pharmaceutically acceptable salts.

28. A method of claim 18 selected from the group consisting of 7-methyl-4H-imidazo-[2,1-c][1,4]-benzoxazine-2-carboxylic acid and its non-toxic, pharmaceutically acceptable salts.

29. A method of claim 18 selected from the group consisting of 8-chloro-7-methyl-4H-imidazo-[2,1-c][1,4]-benzoxazine-2-carboxylic acid and its non-toxic, pharmaceutically acceptable salts.

* * * * *